(12) United States Patent
Schmidt et al.

(10) Patent No.: US 10,589,008 B2
(45) Date of Patent: Mar. 17, 2020

(54) TUBING SET FOR USE IN A BLOOD PROCESSING APPARATUS

(71) Applicant: Fresenius Kabi Deutschland GmbH, Bad Homburg (DE)

(72) Inventors: Frank Schmidt, Schiffweiler (DE); Artur Meisberger, St. Wendel (DE); Melanie Fahrendorff, Troisdorf (DE); Ilka Sternheimer, Frankfurt (DE); Lars Michel, Rosbach v.d.H. (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 354 days.

(21) Appl. No.: 15/503,136

(22) PCT Filed: Aug. 3, 2015

(86) PCT No.: PCT/EP2015/067812
§ 371 (c)(1),
(2) Date: Feb. 10, 2017

(87) PCT Pub. No.: WO2016/030146
PCT Pub. Date: Mar. 3, 2016

(65) Prior Publication Data
US 2017/0224893 A1   Aug. 10, 2017

(30) Foreign Application Priority Data
Aug. 29, 2014 (EP) ..................... 14182870

(51) Int. Cl.
*A61M 1/02* (2006.01)
*A61M 1/36* (2006.01)
(Continued)

(52) U.S. Cl.
CPC ....... *A61M 1/0209* (2013.01); *A61B 5/14535* (2013.01); *A61M 1/0259* (2013.01);
(Continued)

(58) Field of Classification Search
CPC .. A61M 1/0209; A61M 1/3609; A61M 1/361; A61M 1/3612; A61M 1/3632;
(Continued)

(56) References Cited

U.S. PATENT DOCUMENTS 4,484,135 A   11/1984  Ishihara et al.
6,176,903 B1   1/2001  Wamsiedler
(Continued)

FOREIGN PATENT DOCUMENTS

EP   1287839   5/2003
JP   S58-112545   7/1983
(Continued)

OTHER PUBLICATIONS

International Search Report and Written Opinion, counterpart PCT Appl. No. PCT/EP2015/067812, dated Oct. 23, 2015 (10 pages).

*Primary Examiner* — Ariana Zimbouski
(74) *Attorney, Agent, or Firm* — Cook Alex Ltd.

(57) ABSTRACT

A tubing set for use in a blood processing apparatus comprises a measurement device (8) having at least one chamber element (80, 81) for measuring a haematocrit value of a blood fluid, wherein the at least one chamber element (80, 81) extends along a longitudinal axis (L) and comprises a circumferential wall (804, 814) extending about the longitudinal axis (L) and encompassing a flow chamber (802, 812), the at last one chamber element (80, 81) further comprising an inlet port (800, 810) for allowing a flow of a blood fluid into the flow chamber (802, 812) and an outlet port (801, 811) for allowing a flow of a blood fluid out of the flow chamber (802, 812). The tubing set furthermore comprises an inlet-side tube section (21, 31) connected to the inlet port (800, 810) and an outlet-side tube section (22, 30) connected to the outlet port (801, 811). Herein, the inlet port (800, 810) and the outlet port (801, 811) are arranged on the circumferential wall (804, 814) and are displaced with (Continued)

respect to each other along the longitudinal axis (L). In this way a tubing set comprising a measurement device is provided which in an easy and reliable manner allows for the measuring of a haematocrit value of a blood fluid.

14 Claims, 8 Drawing Sheets

(51) Int. Cl.
*A61B 5/145* (2006.01)
*G01N 33/49* (2006.01)
*G01N 29/024* (2006.01)
*G01N 29/22* (2006.01)
*A61M 39/00* (2006.01)

(52) U.S. Cl.
CPC ............ *A61M 1/0281* (2013.01); *A61M 1/36* (2013.01); *A61M 1/361* (2014.02); *A61M 1/3609* (2014.02); *A61M 1/3612* (2014.02); *A61M 1/3632* (2014.02); *A61M 1/3692* (2014.02); *A61M 1/3693* (2013.01); *A61M 39/00* (2013.01); *G01N 29/024* (2013.01); *G01N 29/222* (2013.01); *G01N 33/49* (2013.01); *G01N 33/4915* (2013.01); *A61M 2205/12* (2013.01); *A61M 2205/121* (2013.01); *A61M 2205/3375* (2013.01); *A61M 2209/086* (2013.01); *A61M 2230/207* (2013.01); *G01N 2291/02466* (2013.01)

(58) Field of Classification Search
CPC .............. A61M 1/3692; A61M 1/0259; A61M 1/0281; A61M 1/36; A61M 1/3693; A61M 39/00; A61B 5/14535; G01N 29/024; G01N 29/222; G01N 33/49; G01N 33/4915
See application file for complete search history.

(56) References Cited

U.S. PATENT DOCUMENTS

| | | | |
|---|---|---|---|
| 6,849,039 | B2 | 2/2005 | Min et al. |
| 6,875,191 | B2 | 4/2005 | Smith et al. |
| 6,994,781 | B2 | 2/2006 | Cork et al. |
| 7,748,275 | B2 | 7/2010 | Kouda et al. |
| 7,838,296 | B2 | 11/2010 | Corey et al. |
| 9,517,295 | B2 | 12/2016 | Wilt et al. |
| 9,717,834 | B2 | 8/2017 | Wilt et al. |
| 2003/0042181 | A1 | 3/2003 | Metzner |
| 2005/0230292 | A1 | 10/2005 | Beden et al. |
| 2009/0211987 | A1 | 8/2009 | Min |
| 2010/0133153 | A1* | 6/2010 | Beden ................ A61M 1/1037 210/85 |
| 2011/0269167 | A1 | 11/2011 | Bene |
| 2012/0065568 | A1 | 3/2012 | Law et al. |

FOREIGN PATENT DOCUMENTS

| | | |
|---|---|---|
| JP | H10-080602 | 3/1998 |
| JP | 2004-503756 | 2/2004 |
| JP | 2005-534346 | 11/2005 |
| JP | 2006-503650 | 2/2006 |
| JP | 2006-506607 | 2/2006 |
| JP | 2014-529409 | 11/2014 |
| WO | WO2003/101510 A1 | 12/2003 |
| WO | WO2007/101064 A2 | 9/2007 |
| WO | WO2007/105805 | 9/2007 |
| WO | WO2007/123156 | 11/2007 |
| WO | WO2013/074239 | 5/2013 |

* cited by examiner

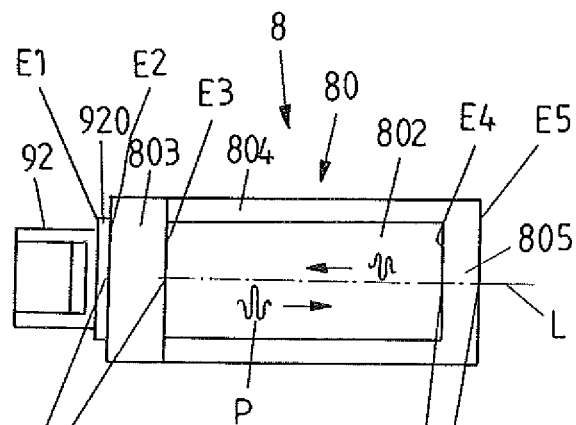
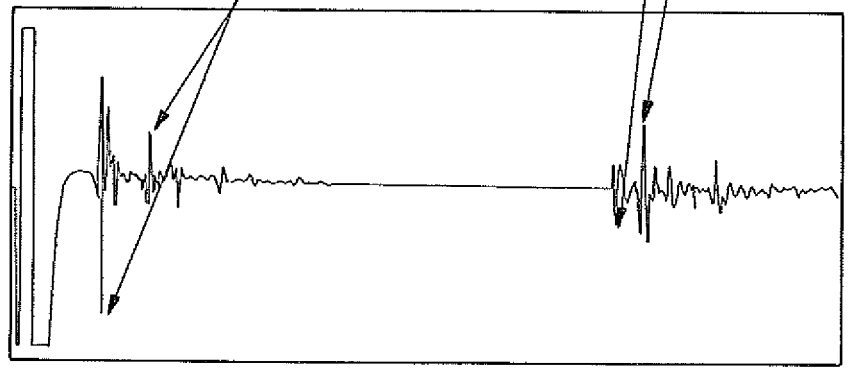

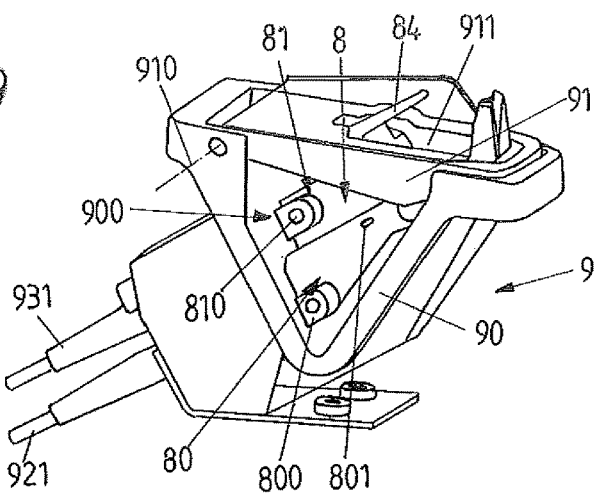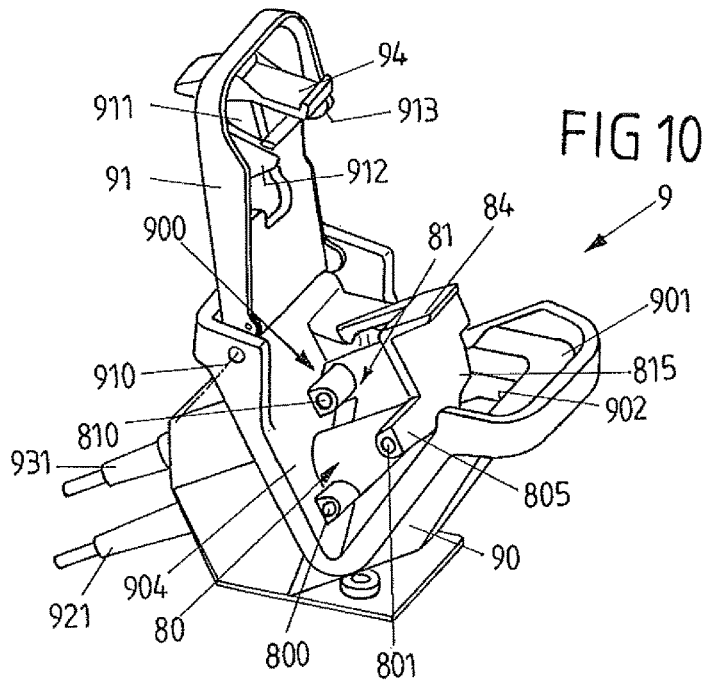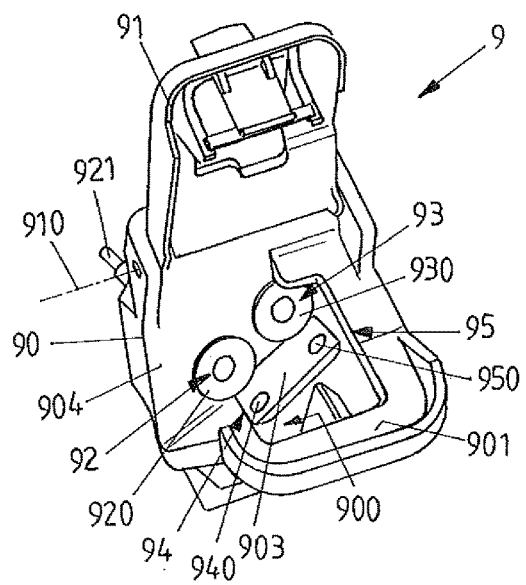

TUBING SET FOR USE IN A BLOOD PROCESSING APPARATUS

The present application is a U.S. National Stage of PCT International Patent Application No. PCT/EP2015/067812, filed Aug. 3, 2015, which claims priority to EP Application No, 14182870.7, filed Aug. 29, 2014, both of which are hereby incorporated herein by reference.

The invention relates to a tubing set for use in a blood processing apparatus according to the preamble of claim 1.

A tubing set of this kind comprises a measurement device having at least one chamber element for measuring a haematocrit value of a blood fluid. The at least one chamber element extends along a longitudinal axis and comprises a circumferential wall extending about the longitudinal axis and encompassing a flow chamber. The at least one chamber element further comprises an inlet port for allowing a flow of a blood fluid into the flow chamber and an outlet port for allowing a flow of a blood fluid out of the flow chamber. An inlet-side tube section is connected to the inlet port, and an outlet-side tube section is connected to the outlet port.

EP 1 287 839 B1 discloses a measurement device comprising a disposable cassette. The disposable cassette is received in a reception chamber of a dialysis apparatus and includes a chamber having an inlet port and an outlet port. A temperature sensor is arranged on the chamber for measuring the temperature of blood contained in the chamber. An ultrasonic transmitter and an ultrasonic transceiver are arranged on opposite sides of the chamber for ultrasonically measuring a haematocrit value of blood contained in the chamber.

WO 2013/074239 A1 discloses an apparatus for measuring a haematocrit value of blood in a specimen.

It is an object of the instant invention to provide a tubing set comprising a measurement device which in an easy and reliable manner allows for the measuring of a haematocrit value of a blood fluid.

This object is achieved by means of a tubing set comprising the features of claim 1.

Accordingly, the inlet port and the outlet port of the chamber element are arranged on the circumferential wall of the chamber element and are displaced with respect to each other along the longitudinal axis.

The inlet port and the outlet port, hence, are arranged on the circumferential wall which extends about the longitudinal axis and encompasses the flow chamber of the chamber element. The inlet port and the outlet port each comprise a conduit opening into the flow chamber of the chamber element and in this way allowing a flow into the flow chamber respectively a flow out of the flow chamber. The inlet port and the outlet port herein open into the flow chamber on the circumferential wall and, because the inlet port and the outlet port are displaced with respect to each other along the longitudinal axis, the inlet port and the outlet port with respect to the longitudinal axis are arranged on different heights.

This makes it possible to provide for a turbulent flow within the flow chamber. Because the blood fluid may flow through the flow chamber in a turbulent fashion, the risk that blood ingredients are deposited within the flow chamber is reduced, thus reducing the risk for effects disturbing a reliable measurement of a haematocrit value.

The flow chamber of the at least one chamber element beneficially has a generally cylindrical shape, wherein the inlet port is arranged close to one end of the cylindrical flow chamber and the outlet port is arranged close to another end of the cylindrical flow chamber.

In one embodiment, the inlet port comprises an inlet conduit extending along a first tangential axis not intersecting with the longitudinal axis. The inlet conduit and the longitudinal axis hence form skew lines which do not intersect, such that a flow through the inlet port is led into the flow chamber not along a radial direction with respect to the longitudinal axis, but along a tangential axis which is displaced from the longitudinal axis.

Likewise, the outlet port may comprise an outlet conduit extending along a second tangential axis which does not intersect with the longitudinal axis such that the second tangential axis and the longitudinal axis form skew lines.

By having the inlet conduit and the outlet conduit form a flow path into respectively out of the flow chamber along tangential axes not intersecting with the longitudinal axis, a turbulent flow within the flow chamber may be generated in a beneficial manner. The inlet conduit and the outlet conduit may open tangentially into the flow chamber with respect to an inner surface of the circumferential wall facing the flow chamber. Through the inlet conduit, hence, a flow is led into the flow chamber along a flow path which is tangential with respect to the inner surface of the circumferential wall encompassing the flow chamber. Likewise, through the outlet conduit the flow is led out of the flow chamber tangentially with respect to the inner surface of the flow chamber.

The inlet conduit and the outlet conduit, in one embodiment, extend in parallel with respect to each other. The first tangential axis defining the flow path of the inlet conduit and the second tangential axis defining the flow path of the outlet conduit hence extend in parallel, wherein both the first tangential axis and the second tangential axis may be arranged in parallel to a transverse direction with respect to the longitudinal axis.

In one embodiment, the first tangential axis and the second tangential axis are displaced with respect to each other in a direction transverse to the longitudinal axis and transverse to both the first and the second tangential axis. The inlet port and the outlet port, hence, are displaced with respect to each other on the circumferential wall not only along the longitudinal axis, but also in a direction transverse to the longitudinal axis.

The inlet port and the outlet port of the chamber element form a connector on which the inlet-side tube section and the outlet-side tube section are fixedly arranged. Herein, the inlet port and the outlet port may be configured to provide for a fastening of the inlet-side tube section and the outlet-side tube section such that the inlet-side tube section and the outlet-side tube section at least at their connection point extend from the circumferential wall in parallel to a direction transverse with respect to the longitudinal axis.

In a particular embodiment, the at least one chamber element comprises a bottom wall and a top wall which, together with the circumferential wall, define the flow chamber enclosed in the chamber element. The bottom wall is arranged on a bottom end of the circumferential wall, whereas the top wall is arranged on a top end of the circumferential wall. The bottom wall and the top wall, hence, are displaced with respect to each other along the longitudinal axis. The inlet port, herein, is arranged on the circumferential wall in the proximity of the bottom wall, whereas the outlet port is arranged on the circumferential wall in the proximity of the top wall.

With respect to an intended use and placement of the chamber element when used in a blood processing apparatus, a blood fluid hence enters the flow chamber through the inlet port at the bottom of the flow chamber, flows through the flow chamber in a turbulent manner and exits the flow chamber through the outlet port at the top of the flow chamber. Because the flow through the flow chamber is effected from the bottom towards the top, air bubbles within the flow chamber may rise to the top and may be washed out from the flow chamber through the outlet port such that air bubbles effectively are removed from the flow chamber. This allows for a measurement within the flow chamber without air bubbles being present such that for example a haematocrit value of a blood fluid may be measured in a reliable manner.

In order to allow for an easy fabrication of the chamber element, the chamber element in one embodiment is made of two separate housing parts which are joined together to form the chamber element. The bottom wall herein may be part of a first housing part, whereas the top wall is part of the second housing part. Both housing parts may be fabricated for example from plastics by injection molding. Upon joining the housing parts together, the chamber element with the flow chamber enclosed therein is formed.

The chamber element, in particular the circumferential wall of the chamber element, may for example be formed of a polymer, in particular a polycarbonate.

In one embodiment, the circumferential wall of the at least one chamber element comprises, at an outer side facing away from the flow chamber, a flat face which may be adapted for positioning an infrared sensor element on the at least one chamber element. The infrared sensor element serves to measure a temperature of a blood fluid contained in the flow chamber, wherein for this purpose it may be advantageous that the flat face comprises a reduced wall thickness as compared to other portions of the circumferential wall. By means of the circumferential wall having a small wall thickness in the area of the flat face it is achieved that the temperature of a blood fluid contained in the flow chamber may be reliably measured by an infrared sensor located outside the flow chamber. If the wall thickness of the circumferential wall at the flat face is thin, the temperature at the flat face will at least approximately match the inner temperature of the flow chamber. By measuring the temperature at the flat face using an infrared sensor, hence, a reliable temperature measurement for the blood fluid contained in the flow chamber may be obtained.

By means of an infrared sensor element a temperature measurement may be conducted in a contactless fashion by receiving infrared radiation emitted from the flat face of the chamber element.

In order to allow for an easy handling of the tubing set, the measurement device may comprise a handle via which a user may manually grab the measurement device. By grabbing the measurement device on the handle, the measurement device for example can be inserted into a holder device of a blood processing apparatus and hence may be fixed on the blood processing apparatus. Via the handle the measurement device may also be grabbed to remove it from the blood processing apparatus to dispose the tubing set.

In one embodiment, the measurement device comprises a first chamber element and a second chamber element. The first chamber element and the second chamber element are connected to each other and hence form an integral unit. The first chamber element herein may be connected to a first inlet-side tube section and a first outlet-side tube section, and the second chamber element may be connected to a second inlet-side tube section and a second outlet-side tube section. Via the two chamber elements independent measurements on two blood flows, for example of a blood flow entering the blood processing apparatus and a blood flow exiting the blood processing apparatus, may be performed. The chamber elements may for example each have a generally cylindrical shape and each may extend along a longitudinal axis, wherein the longitudinal axes of the chamber elements may run in parallel to each other. By connecting the chamber elements to each other via webs, it can be made sure that independent measurements within the chamber elements can be obtained, without the flow through the first chamber element affecting the flow through the second chamber element.

The idea underlying the invention shall subsequently be described in more detail with regard to the embodiments shown in the figures. Herein:

FIG. 4 shows a schematic view of a chamber element of a measurement device;

FIG. 5 shows a sensor signal received at a sensor element for measuring a haematocrit value of a blood fluid contained in the chamber element;

FIG. 9 shows a perspective view of a holder device of the blood processing apparatus with a measurement device received therein;

FIG. 10 shows a perspective view of the holder device with a closure element in an opened position;

FIG. 11 shows a perspective view of the holder device, without a measurement device received therein;

FIG. 1 shows a blood processing apparatus 1 which may be constituted for example as a so-called continuous autotransfusion system (CATS).

An autotransfusion system may serve to collect blood from a patient for example during or after a surgical operation. The collected blood is processed within the autotransfusion system and is recycled in order to re-transfuse it into the patient.

Figure 1:
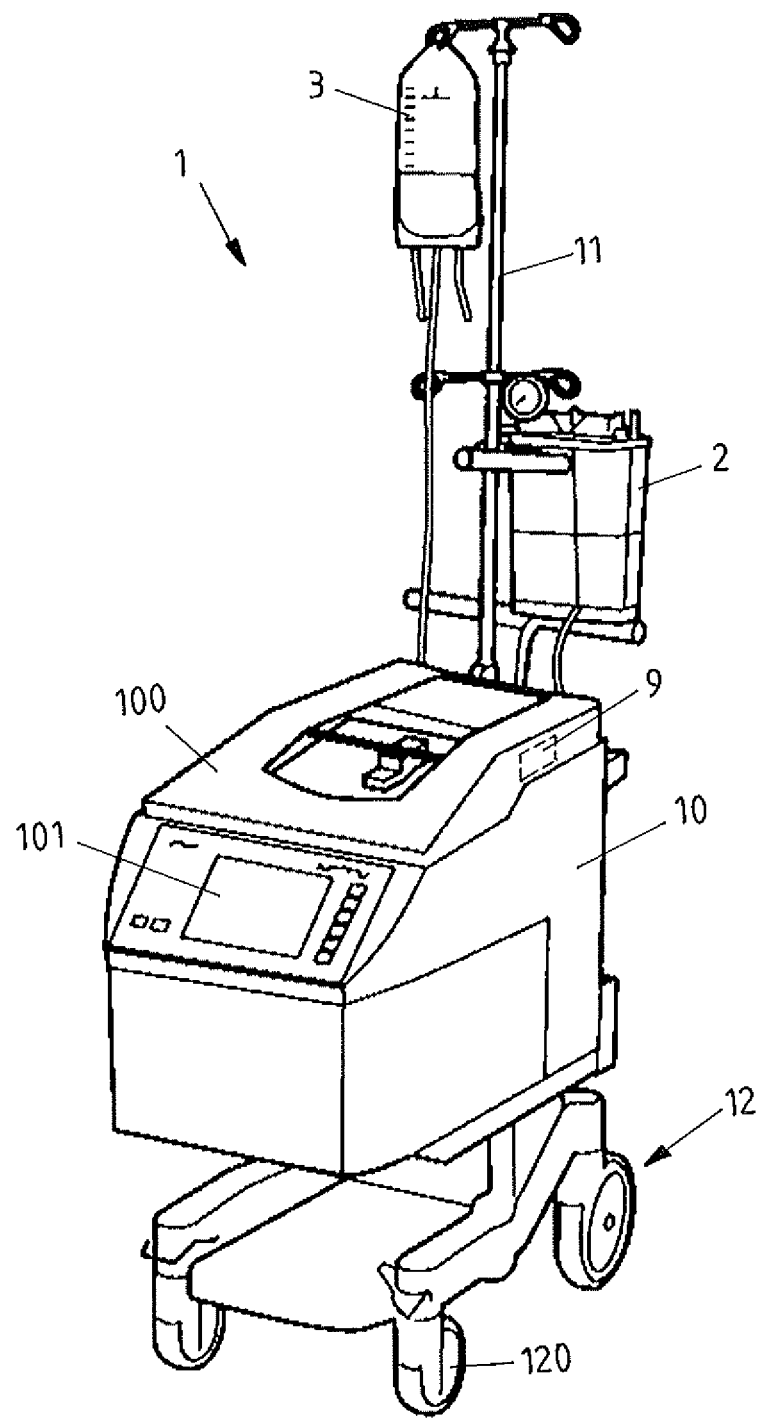
FIG. 1 shows a blood processing apparatus.

The blood processing apparatus 1 of FIG. 1 constituting an autotransfusion system for this purpose comprises a first reservoir container 2 for collecting blood from a patient. Through a tubing set the blood is guided from the reservoir container 2 to a washing chamber 7 (see FIGS. 2 and 3) contained in a housing 10 of the blood processing apparatus 1, by means of which the blood is processed and, after processing, collected in a second reservoir container 3 constituting a so-called re-transfusion bag, from which the blood may be re-transfused to the patient.

In the example of FIG. 1, the housing 10 comprises a lid 100 which may be opened in order to access the washing chamber 7 contained in the housing 10 and to arrange the tubing set within the housing 10 in a suitable manner. The housing 10 furthermore comprises a control panel 101 via which control commands for operating the blood processing apparatus 1 may be entered.

The housing 10 is arranged on a base 12 comprising wheels 120 such that the blood processing apparatus 1 is mobile for example in an operating theatre of a hospital.

From the housing 10 a stand 11 extends vertically on which the first reservoir container 2 for collecting the patient's blood and a second reservoir container 3 for collecting the processed blood for re-transfusing it to the patient are arranged.

On the stand 11 further containers, such as a bag for a washing solution 4 (see FIGS. 2 and 3), may be arranged.

Figure 2:
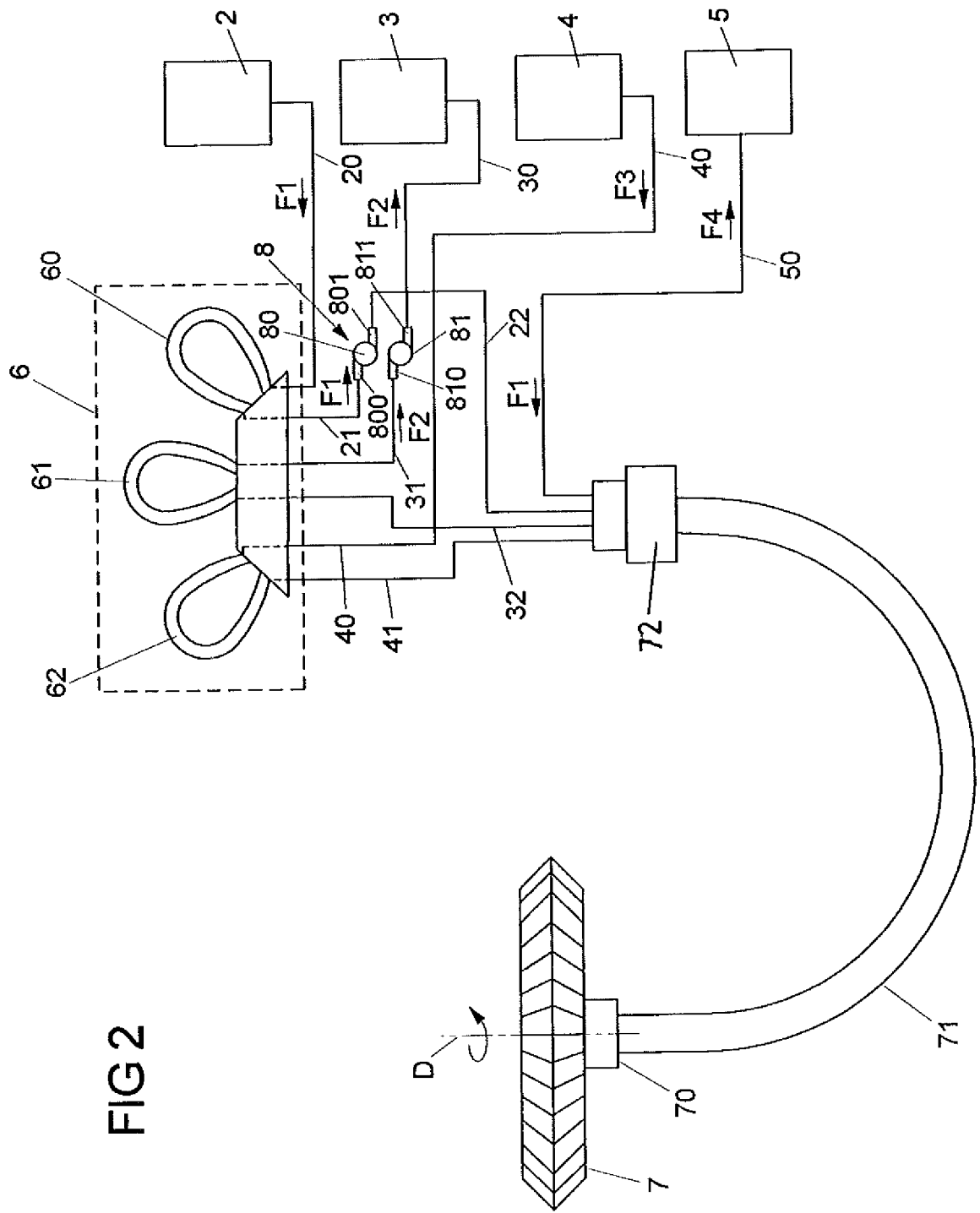
FIG. 2 shows a schematic drawing of a tube set used with a blood processing apparatus.
Figure 3:
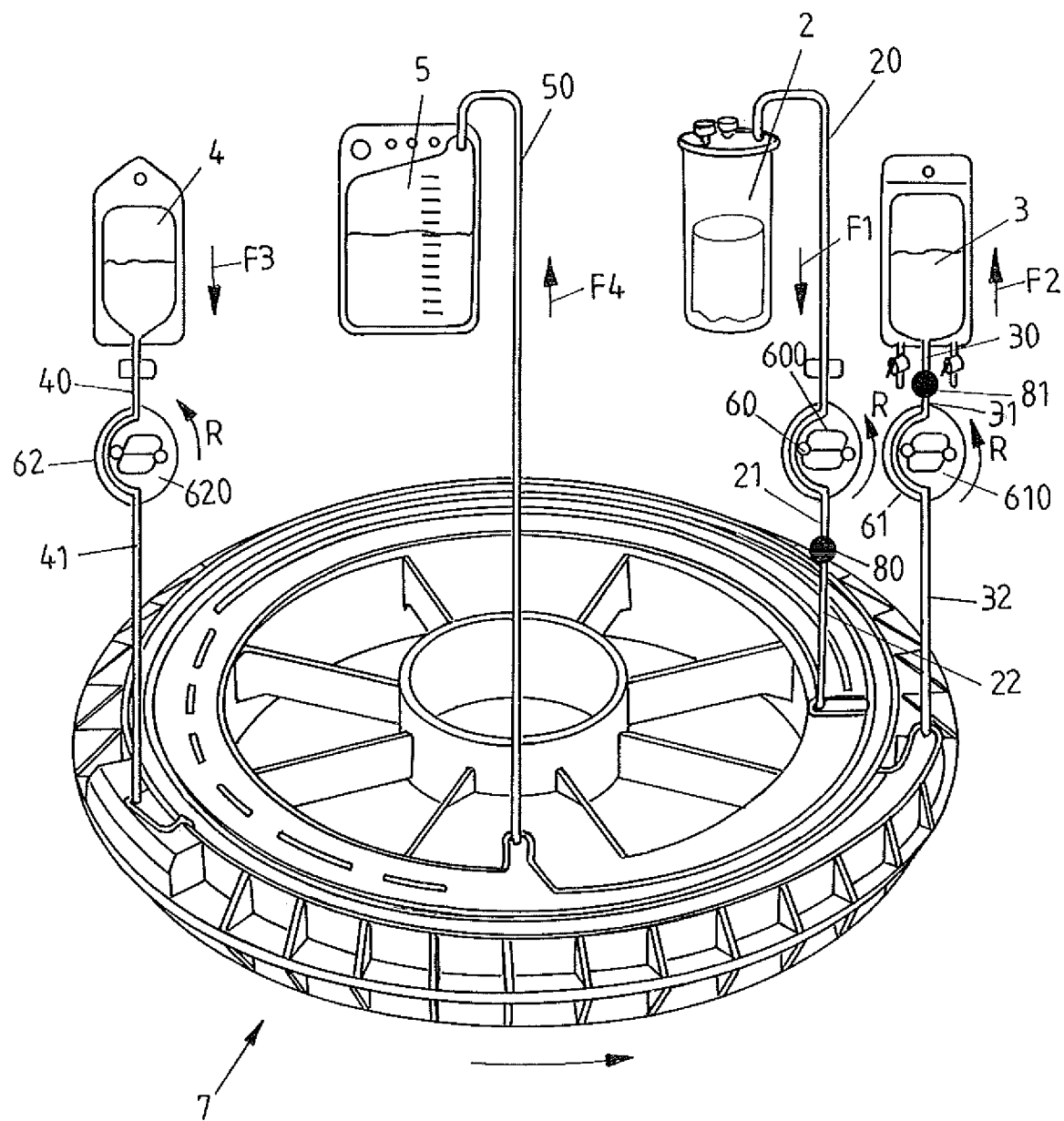
FIG. 3 shows a schematic drawing of the tubing set in relation to a washing chamber of the blood processing apparatus.

The functional setup of the blood processing apparatus 1 is as shown in FIGS. 2 and 3.

The washing chamber 7 contained in the housing 10 is rotatable about a rotational axis D and, during operation of the blood processing apparatus 1, is rotated about the rotational axis D in order to perform a centrifugation process within the washing chamber 7. The washing chamber 7 comprises a connector 70 from which a conduit 71 extends towards another connector 72.

As functionally shown in FIG. 3, the first reservoir container 2 containing blood collected from the patient, the second reservoir container 3 constituting a re-transfusion bag for re-transfusing blood to the patient, a bag for a washing solution 4, in particular a saline solution, and a waste bag 5 via a tubing set comprising different tube sections are connected to the washing chamber 7. The different tube sections herein are effectively connected at different locations on the washing chamber 7, as shown in FIG. 3.

As shown in FIG. 3, the first reservoir container 2 via a tube section 20 is connected to a tube segment 60 on which a peristaltic pump mechanism 600 acts. By means of the pump mechanism 600 a flow from the reservoir container 2 is caused through a tube section 21 via a chamber element 81 of a measurement device 8 and a tube section 22 towards the washing chamber 7.

The second reservoir container 3 is connected via a tube section 30 to a chamber element 81 of the measurement device 8 and via a tube section 31 to a tube segment 61 on which a second peristaltic pump mechanism 610 acts. The tube segment 61 via a tube section 32 is connected to the washing chamber 7.

The bag of the washing solution 4 is connected via a tube section 40 to a tube segment 62 on which a third peristaltic pump mechanism 620 acts. The tube segment 62 is connected via a tube section 41 to the washing chamber 7.

The pump mechanisms 600, 610, 620 each are constituted to perform a peristaltic pump action. For this, each pump mechanism 600, 610, 620 during operation of the blood processing apparatus 1 performs a rotational movement R and through this rotational movement R acts on the respective tube segment 60, 61, 62.

The pump mechanism 600 acting on the tube segment 60 connected to the first reservoir container 2 and likewise the pump mechanism 620 acting on the tube segment 62 connected to the bag for the washing solution 4 cause a flow in a flow direction F1, F3 towards the washing chamber 7 such that blood from the first reservoir container 2 and a washing solution from the bag 4 are transported towards the washing chamber 7.

The pump mechanism 610 acting on the tube segment 61 connected to the second reservoir container 3 for collecting processed blood for re-transfusing it to the patient, in contrast, causes a flow in a flow direction F2 from the washing chamber 7 towards the second reservoir container 3.

The waste bag 5 is connected via a tube section 50 directly to the washing chamber 7, without a pump mechanism acting on the tube section 50. During operation of the blood processing apparatus 1 a flow in a flow direction F4 from the washing chamber 7 towards the waste bag 5 is caused.

As schematically shown in FIG. 2, the tube segments 60, 61, 62, on which the three pump mechanisms 600, 610, 620 act, are arranged in a pump bed 6 in a manner known per se.

During operation of the blood processing apparatus 1 blood is transported from the reservoir container 2 into the washing chamber 7 and is processed within the washing chamber 7 in order to recycle and collect it for re-transfusion in the reservoir container 3. The processing herein takes place in the washing chamber 7 in different phases.

In a first phase—the so-called first separation phase—blood enters from the reservoir container 2 into the washing chamber 7 by pumping action of the pump mechanism 600 delivering the blood through the tube sections 20-22. In this initial separation stage, the blood is concentrated to a haematocrit value of approximately 80% within the washing chamber 7, and most of the blood plasma, cellular debris, white blood cells, platelets, anti-coagulant and other unwanted constituents are separated out and flow through the tube section 50 into the waste bag 5. This separation is effected by the rotary movement of the washing chamber 7 causing a centrifugation and, hence, a separation of the blood into its different components.

During a second phase—the so-called washing phase—the remaining constituents of the blood, in particular red blood cells, are re-suspended with a washing solution, for example a saline solution delivered from the bag for the washing solution 4 through tube sections 40, 41 by the pumping action of the pump mechanism 620. In the washing phase also a further removal of blood plasma occurs.

In a third phase—the so-called second separation phase—a final separation takes place. In this phase, the red blood cells are packed to a haematocrit value concentration of about 60 to 65%. During this phase the saline solution added during the washing phase is again removed.

The blood processed in this way leaves the washing chamber 7 through tube sections 32, 31, 30 and, by means of the pumping action of the pump mechanism 610, is pumped into the reservoir container 3 where it is collected for re-transfusion into the patient.

As shown in FIG. 2, a measurement device 8 is placed within the tubing set. The measurement device 8 serves to determine the haematocrit value in the blood flowing from the reservoir container 2 towards the washing chamber 7 and in the blood exiting the washing chamber 7 and flowing towards the reservoir container 3 for collecting the processed blood for re-transfusion. The measurement device 8 comprises two chamber elements 80, 81, each having an inlet port 800, 810 and an outlet port 801, 811.

The reservoir container 2 via its tube sections 20, 21 is connected to the inlet port 800 of the first chamber element 80, whereas the outlet port 801 of the first chamber element 80 is connected via the tube section 2 to the washing chamber 7. The washing chamber 7 in turn is connected via the tube sections 32, 31 to the inlet port 810 of the second chamber element 81, wherein the outlet port 811 of the second chamber element 81 via the tube section 30 is connected to the reservoir container 3.

As depicted in FIG. 3, the chamber elements 80, 81 of the measurement device 8 in each case are arranged downstream from the respective pump mechanism 600, 610. In particular, the pump mechanism 600 causing the flow from the reservoir container 2 towards the washing chamber 7 is arranged upstream of the inlet port 800 of the first chamber element 80. The pump mechanism 610 for delivering the processed blood into the reservoir container 3 for re-transfusing the processed blood into the patient is arranged upstream of the inlet port 810 of the second chamber element 81.

Because the chamber elements 80, 81 each are arranged downstream from the pump mechanism 600, 610, each chamber element 80, 81 is arranged on the pressure side of the respective pump mechanism 600, 610. This has the beneficial effect that cavitation effects, as they may occur upstream the pump mechanism 600, 610 due to a negative pressure created upstream by suction of the pump mechanism 600, 610, can be reduced to a minimum such that such cavitation effects do not impact measurements within the chamber elements 80, 81.

The measurement device 8 with its chamber elements 80, 81 serves to measure the haematocrit value of the blood flowing from the reservoir container 2 into the washing chamber 7 and from the washing chamber 7 into the reservoir container 3. Measuring the haematocrit value within the blood flowing from the reservoir container 2 towards the washing chamber 7 allows for controlling the process dependent on the haematocrit of the blood streaming into the washing chamber 7. Measuring the haematocrit in the processed blood flowing from the washing chamber 7 towards the reservoir container 3 provides information about the processed blood and the haematocrit obtained therein and allows for an adjustment of process parameters to obtain a desired haematocrit value.

The measurement device 8 with its chamber elements 80, 81, as mentioned, serves to measure the haematocrit value of blood flowing through the chamber elements 80, 81. The measurement herein is carried out, as shown in FIGS. 4 and 5, by transmitting ultrasonic pulses P from an ultrasonic sensor element 92 into an associated chamber element 80, 81 and by receiving reflection signals occurring within the chamber element 80, 81. By examining the propagation times of pulses P within the chamber element 80, 81, the density of the blood contained in the chamber element 80, 81 can be analyzed and the haematocrit of the blood can be derived.

As shown in FIG. 6 and FIG. 7A to 7C, each chamber element 80, 81 has a generally cylindrical shape. Each chamber element 80, 81 comprises a bottom wall 803, 813, a circumferential wall 804, 814 and a top wall 805, 815. The bottom wall 803, 813, the circumferential wall 804, 814 and the top wall 805, 815 together define a flow chamber 802, 812 through which the blood flows.

Returning to FIG. 4, an ultrasonic sensor element 92 is arranged on the bottom wall 803 of the chamber element 80 and is coupled to the bottom wall 803 via a coupling pad 920. The ultrasonic sensor element 92 is constituted to emit ultrasonic pulses P generally along a longitudinal axis L along which the chamber element 80 with its flow chamber 802 contained therein extends.

As shown in the curve of FIG. 5, when emitting an ultrasonic pulse P into the chamber element 80, reflections occur at different faces E1-E5 of the chamber element 80.

In particular, a first reflection occurs at a face E2 inbetween the coupling pad 920 and the bottom wall 803. A second reflection occurs at the face E3 of the bottom wall 803 towards the flow chamber 802. A third reflection occurs at the face E4 of the top wall 805 towards the flow chamber 802. And a fourth reflection occurs at the face E5 of the top wall 805 towards the outside.

Such reflections may be recorded in the ultrasonic sensor element 92, and from the recorded reflections the propagation times may be measured. If the geometry of the chamber element 80 is known, the densities of the materials through which the pulse P has propagated can be concluded. From the density of the blood in the flow chamber 802, then, the haematocrit value of the blood contained in the flow chamber 802 can be derived.

In order to calibrate the measurement device 8, an initial measurement may be taken by using a saline solution having a known density in order to derive the length of the different paths of the chamber element 80.

The length of the different paths in the chamber element 80 should be chosen such that reflections at the different faces E1-E5 can be discerned in a reliable manner. For this, the thickness of the bottom wall 803 and the top wall 805 and the length of the flow chamber 802 along the longitudinal axis L should be chosen appropriately.

The coupling pad 920 serves to obtain a beneficial coupling of the sensor element 92 to the bottom wall 803 of the chamber element 80. As will be described later, it may be suitable to press the chamber element 80 with its bottom wall 803 against the coupling pad 920 with a suitable force (for example exceeding 15 N).

Figure 6:
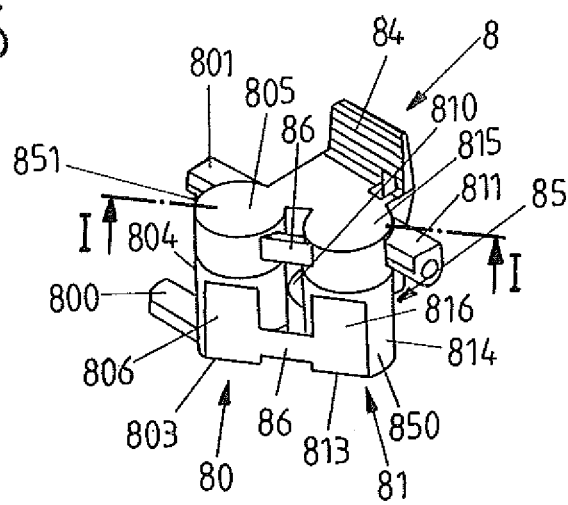
FIG. 6 shows a perspective view of an embodiment of a measurement device comprising two chamber elements.
Figure 7A:
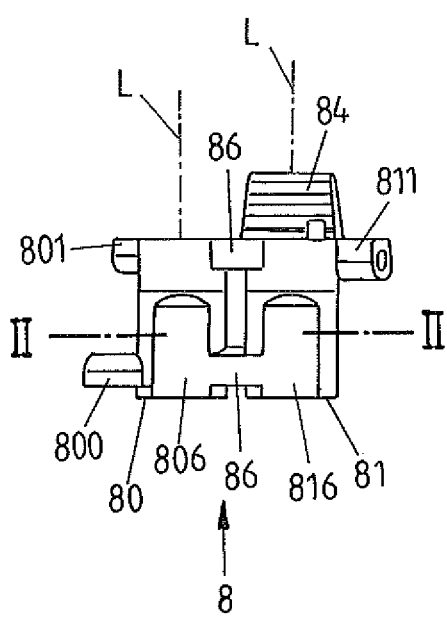
FIG. 7A shows a side view of the measurement device according to FIG. 6.
Figure 7B:
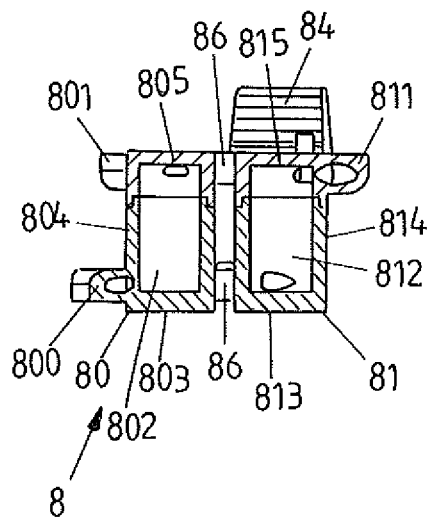
FIG. 7B shows a sectional view of the measurement device along the line I-I according to FIG. 6.
Figure 7C:
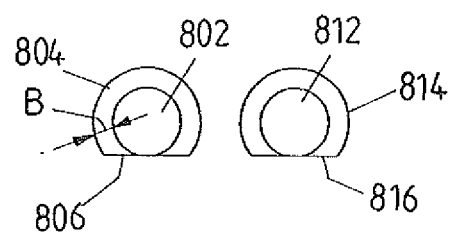
FIG. 7C shows a sectional view of the measurement device along the line II-II according to FIG. 7A.

FIGS. 6 and 7A, 7B show an embodiment of a measurement device 8 comprising two chamber elements 80, 81 integrally connected to each other via webs 86 to form an integral measurement unit. The measurement device 8 herein is fabricated from two housing parts 850, 851 to form a housing 85. The housing parts 850, 851 may be separately fabricated for example by injection molding from a plastics material, for example a polymer such as polycarbonate, and may subsequently be joined together to form the measurement device 8.

Each chamber element 80, 81 extends longitudinally along a longitudinal axis L. The longitudinal axes L of the chamber elements 80, 81 herein extend in parallel with respect to each other. Each chamber element 80, 81 comprises a circumferential wall 804, 814 circumferentially extending about the respective longitudinal axis L such that two generally cylindrical chamber elements 80, 81 are formed.

Each chamber element 80, 81 comprises an inlet port 800, 810 and an outlet port 801, 811. The inlet port 800, 810, in each case, is arranged in the vicinity of the bottom wall 803, 813, whereas the outlet port 801, 811 in each case is arranged in the vicinity of the top wall 805, 815.

As shown in FIG. 7B, the inlet ports 800, 810 open into the respective flow chamber 802, 812 immediately inside the bottom wall 803, 813, whereas the outlet ports 801, 811 open into the respective flow chamber immediately inside the top wall 805, 815.

As shown in FIG. 7A, the inlet port 800, 810 and the outlet port 801, 811 for each chamber element 80, 81 are arranged on the circumferential wall 804, 814 of the respective chamber element 80, 81 and are displaced with respect to each other along the longitudinal axis L. The inlet port 800, 810 and the outlet port 801, 811 hence are arranged at different heights with respect to the longitudinal axis L.

Figure 8A:
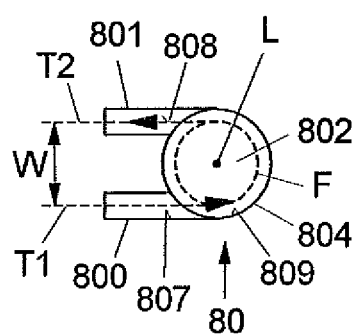
FIG. 8A shows a schematic top view of a first chamber element of the measurement device.
Figure 8B:
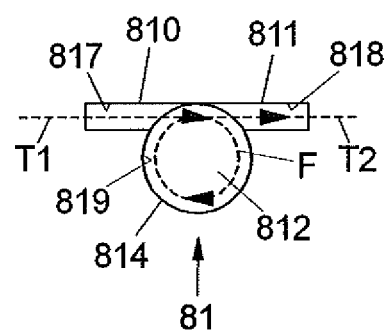
FIG. 8B shows a schematic top view of a second chamber element of the measurement device.

Furthermore, as schematically illustrated in FIG. 8A for the first chamber element 80 and in FIG. 8B for the second chamber element 81, the inlet port 800, 810 and the outlet port 801, 811 each comprise a conduit 807, 808, 817, 818 for allowing a flow into the flow chamber 802, 812 respectively out of the flow chamber 802, 812. The conduits 807, 808, 817, 818 extend along tangential axes T1, T2 which do not intersect with the longitudinal axis L and hence form skew lines with the longitudinal axis L.

In particular, the conduit 807 of the inlet port 800 of the first chamber element 80 extends along a first tangential axis T1 not intersecting with the longitudinal axis L, as shown in FIG. 8A. Likewise, the conduit 808 of the outlet port 801 of the first chamber element 80 extends along a second tangential axis T2, which runs in parallel to the first tangential axis T1 and is displaced by a displacement W from the first tangential axis T1.

For the first chamber element 80, blood flows into the flow chamber 802 in a first direction and leaves the flow chamber 802 through the outlet port 801 in an opposite, second direction. Due to the conduits 807, 808 extending along the tangential directions T1, T2, the inlet port 800 and the outlet port 801 open tangentially into the flow chamber 802 such that the flow F enters the flow chamber 802 tangentially with respect to an inner surface 809 of the flow chamber 802 and, likewise, tangentially exits the flow chamber 802 through the outlet port 801.

In combination with the displacement of the inlet port 800 and the outlet port 801 along the longitudinal axis L, this causes a turbulent flow F within the flow chamber 802, as it is illustrated in FIG. 8A. Such turbulent flow F reduces the risk for depositions within the flow chamber 802.

As shown in FIG. 8B for the second chamber element 81, the conduits 817, 818 of the inlet port 810 and the outlet port 811 of the second chamber element 81 likewise open tangentially into the flow chamber 812 to cause a turbulent flow F in the flow chamber 812. Herein, the tangential axes T1, T2 are in line with each other (when viewed from the top), but the inlet port 810 and the outlet port 811 extend towards different sides from the circumferential wall 814 of the second chamber element 81.

Figure 8C:
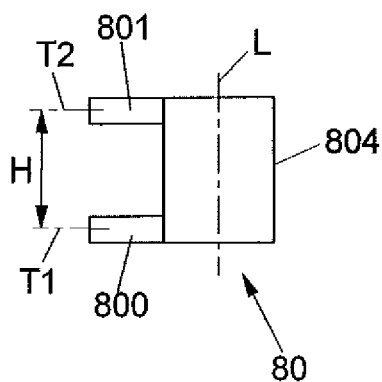
FIG. 8C shows a schematic side view of the first chamber element of the measurement device.
Figure 8D:
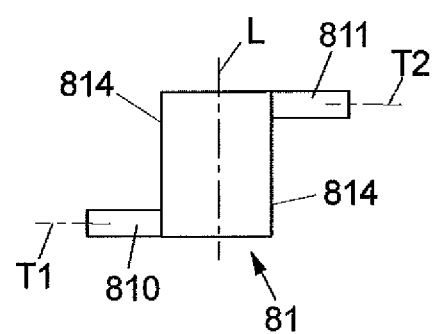
FIG. 8D shows a schematic side view of the second chamber element of the measurement device.

FIGS. 8C and 8D illustrate the longitudinal displacement of the inlet port 800, 810 and the outlet port 801, 811 for the different chamber elements 80, 81 along the respective longitudinal axis L. For both chamber elements 80, 81 the tangential axes T1, T2 along which the inlet port 800, 810 and the outlet port 801, 811 extend are displaced with respect to each other by a displacement H.

As visible from FIGS. 6 and 7A, each chamber element 80, 81 at the outside of its circumferential wall 804, 814 comprises a flat face 806, 816, the flat faces 806, 816 being aligned such that they lie in the same plane. As visible from the sectional drawing of FIG. 7C, in the region of the flat face 806, 816 the circumferential wall 804, 814 comprises a reduced wall thickness B.

The flat face 806, 816 of each chamber element 80, 81 serves for interaction with an infrared sensor element, as will be described later. Via the flat face 806, 816 the temperature inside the flow chamber 802, 812 may be measured by receiving infrared radiation emitted from the flat face 806, 816.

The measurement device 8 comprises a handle 84 for manually grabbing the measurement device 8. The handle 84 is arranged on the housing part 851 forming the top walls 805, 815 of the chamber elements 80, 81.

The measurement device 8 is part of the tubing set formed by the tube sections connecting the reservoir container 2, the reservoir container 3, the bag for the washing solution 4 and the waste bag 5 to the washing chamber 7. In particular, an autotransfusion set may be disposable and may consist of the washing chamber 7 and all tube sections for connecting the washing chamber 7 with the respective bags or containers 2-5, including the tube segments 60-62 interacting with the pump mechanisms 600-620.

The blood processing apparatus 1, as schematically shown in FIG. 1, receives in its housing 10 the washing chamber 7 and comprises a holder device 9 for receiving the measurement device 8. An embodiment of such a holder device 9 is shown in FIGS. 9 to 11.

The holder device 9 in the embodiment of FIGS. 9 to 11 comprises a base 90 and a closure element 91 which is arranged on the base 90 and is pivotable about a pivoting axis 910 with respect to the base 90. The base 90 forms a reception opening 900 into which the measurement device 8 with its chamber elements 80, 81 may be inserted such that, in an inserted position shown in FIGS. 9 and 10, the measurement device 8 is received in the reception opening 900.

Figure 12:
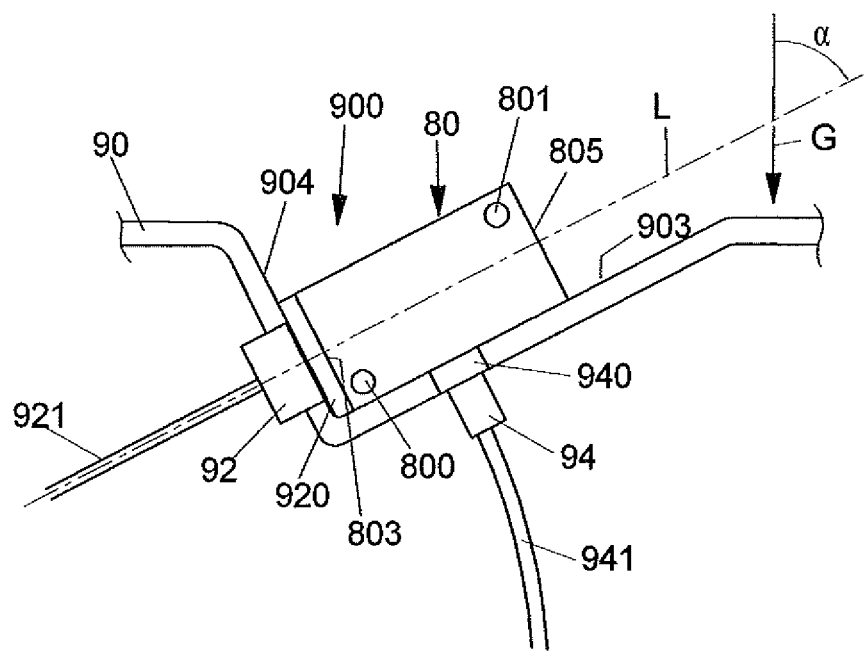
FIG. 12 shows a schematic view of the holder device in relation to a measurement device.

The base 90 comprises, as shown in FIG. 11 and as schematically illustrated in FIG. 12, a first tilted face 904 and a second tilted face 903. The tilted faces 903, 904 are arranged perpendicularly to each other and serve to abut the bottom walls 803, 813 respectively flat faces 806, 816 of the circumferential walls 804, 814 of the chamber elements 80, 81.

Herein, at the first tilted face 904 two ultrasonic sensor elements 92, 93 are arranged which comprise coupling pads 920, 930 and face with their coupling pads 920, 930 towards the outside. At the second tilted face 903 two infrared windows 940, 950 are arranged which are (at least partially) transparent for infrared radiation and form windows for infrared sensors 94, 95 located behind the infrared windows 940, 950, as schematically shown in FIG. 12.

In its inserted position the measurement device 8 with its chamber elements 80, 81 is inserted into the reception opening 900 such that the bottom walls 803, 813 of the chamber elements 80, 81 face the first tilted face 904 and are in contact with the coupling pads 920, 930. At the same time, the chamber elements 80, 81 with the flat faces 806, 816 abut the second tilted face 903 such that the flat face 806 of the first chamber element 80 faces the infrared window 940 and the flat face 816 of the second chamber element 81 faces the infrared window 950.

For inserting the measurement device 8 into the reception opening 900, the closure element 91 may be opened, as it is shown in FIGS. 10 and 11. After inserting the measurement device 8 into the reception opening 900, the closure element 91 is closed, as shown in FIG. 9, such that a front edge of the closure element 91 comes to lie at an edge section 901 of the base 90. In the closed position the closure element 91 via a locking element 914 is locked with respect to the base 90 in that the locking element 914 engages a corresponding locking element 902 of the base 90 such that a positive locking between the closure element 91 and the base 90 is achieved.

In the closed position of the closure element 91 fixing elements 912, 913 protruding from the inner face of the closure element 91 facing the inside of the reception opening 900 abut the chamber elements 80, 81 at their top walls 805, 815. By means of the fixing elements 912, 913 a force is exerted on the chamber elements 80, 81 along the longitudinal axis L such that the chamber elements 80, 81 are pressed with a predefined force against the coupling pads 920, 930 of the ultrasonic sensor elements 92, 93. In this way, a beneficial coupling of the sensor elements 92, 93 to the bottom walls 803, 813 of the chamber elements 80, 81 is achieved.

Figure 13:
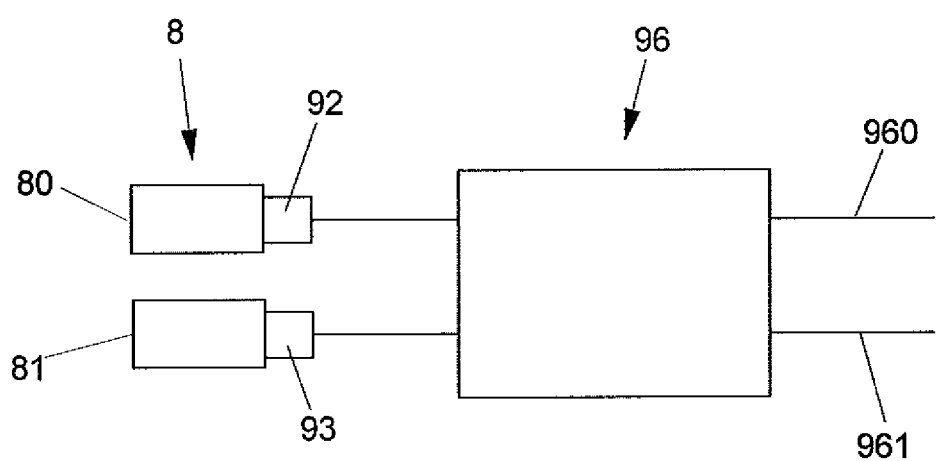
FIG. 13 shows a schematic view of a control circuit connected to ultrasonic sensor elements of the holder device.

As shown in FIGS. 9 and 10, connecting lines 921, 931 are connected to the sensor elements 92, 93 and serve to electrically connect the sensor elements 92, 93 to a control unit 96, as it is shown in FIG. 13. Via the connecting lines 921, 931 the sensor elements 92, 93 are excited to produce ultrasonic pulses P, and reflection signals received at the sensor elements 92, 93 are transmitted as sensor signals to the control unit 96.

In the control unit 96 a signal processing takes place in order to determine a haematocrit value of the blood flowing through the respective chamber element 80, 81. The control unit 96 comprises a power line 960 for electrically feeding the control unit 96 and a data output line 961 for providing data to other units.

The infrared sensor elements 94, 95 are used to determine a temperature of blood in the chamber elements 80, 81. As sown in FIG. 12, each infrared sensor element 94, 95 may be connected to a connecting line 941 (shown in FIG. 12 only for the infrared sensor element 94) for transmitting sensor signals to the control unit 96.

As shown in FIG. 12, the chamber elements 80, 81 with their longitudinal axes L are arranged at an angle α with respect to the direction of gravity G. Because the outlet port 801, 811 for each chamber element 80, 81 is arranged at the top wall 805, 815 of the respective chamber element 80, 81, air bubbles within the flow chamber 802, 812 may rise in the flow chamber 802, 812 and may be washed out through the respective outlet port 801, 811 such that the air bubbles are removed from the flow chamber 802, 812. Hence, measurements within the chamber element 80, 81 are not disturbed by the presence of air bubbles.

The outlet port 801, 811 for each chamber element 80, 81, when inserted into the holder device 9, herein beneficially is arranged at the highest point of the flow chamber 802, 812 with respect to the direction of gravity G, as it is illustrated in FIG. 12. This ensures that air bubbles rising in the flow chamber 802, 812 against the direction of gravity G may exit the flow chamber 802, 812 through the outlet port 801, 811 and are not caught within the flow chamber 802, 812.

The closure element 91 comprises an opening 911 through which the handle 84 extends when the measurement device 8 is inserted into the reception opening 900 and the closure element 91 is closed, as it is shown in FIG. 9. A user hence may hold the measurement device 8 by grabbing the handle 84 until the closure element 91 is fully closed, which makes it easy to insert the measurement device 8 in a correct manner into the holder device 9.

The holder device 9 beneficially is constituted such that the measurement device 8 may be inserted into the reception opening 900 only in a single position. This ensures that the measurement device 8 is inserted correctly into the holder device 9 even by untrained users.

The idea underlying the invention is not limited to the embodiments described above, but may be used also in entirely different embodiments.

In particular, the invention is not limited to autotransfusion systems, but may be used also within other medical systems for processing blood.

LIST OF REFERENCE NUMERALS

1 Blood processing apparatus
10 Housing
100 Lid
101 Control panel
11 Stand
12 Base
120 Wheels
2 Reservoir container
20-22 Tube section
3 Re-transfusion bag
30-32 Tube section
4 Bag for washing solution
40, 41 Tube section
5 Waste bag
50 Connection tube
6 Pump bed
60-62 Tube segment
600-620 Pump mechanism
7 Washing chamber
70 Connector
71 Conduit
72 Connector
8 Measurement device
80, 81 Chamber element
800, 810 Inlet port
801, 811 Outlet port
802, 812 Flow chamber
803, 813 Bottom wall
804, 814 Circumferential wall
805, 815 Top wall
806, 816 Flat face
807, 817 Conduit
808, 818 Conduit
809, 819 Inner surface
84 Handle
85 Housing
850, 851 Housing part
86 Webs
9 Holder device
90 Base
900 Reception opening
901 Edge section
902 Locking element
903, 904 Tilted face
91 Closure element
910 Pivoting axis
911 Opening
912, 913 Fixing element
914 Locking element
92, 93 Ultrasonic sensor element
920, 930 Coupling pad
921, 931 Connecting line
94, 95 Infrared sensor element
940, 950 Infrared window
941, 951 Connection
96 Control unit
960, 961 Connections
α Angle
B Wall thickness
D Rotational axis
E2-E5 Face
F Flow
F1-F4 Flow direction
G Direction of gravity
H Height
L Longitudinal axis
P Pulse R Rotational movement
T1, T2 Tangential axis
W Width

The invention claimed is:

1. A tubing set for use in a blood processing apparatus, comprising:
a measurement device having at least one chamber element for measuring a haematocrit value of a blood fluid, wherein the at least one chamber element extends along a longitudinal axis and comprises a circumferential wall extending about the longitudinal axis and encompassing a flow chamber, the at last one chamber element further comprising an inlet port for allowing a flow of a blood fluid into the flow chamber and an outlet port for allowing a flow of a blood fluid out of the flow chamber,
an inlet-side tube section connected to the inlet port, and an outlet-side tube section connected to the outlet port,
wherein the inlet port and the outlet port are arranged on the circumferential wall and are displaced with respect to each other along the longitudinal axis, wherein the inlet-side tube section and the outlet-side tube section extend from the circumferential wall transversely with respect to the longitudinal axis.

2. The tubing set according to claim 1, wherein the flow chamber has a cylindrical shape.

3. The tubing set according to claim 1, wherein the inlet port comprises an inlet conduit extending along a first tangential axis not intersecting with the longitudinal axis and/or the outlet port comprises an outlet conduit extending along a second tangential axis not intersecting with the longitudinal axis.

4. The tubing set according to claim 3, wherein the inlet conduit opens tangentially, with respect to an inner surface of the circumferential wall facing the flow chamber, into the flow chamber and/or the outlet conduit opens tangentially, with respect to the inner surface of the circumferential wall facing the flow chamber, into the flow chamber.

5. The tubing set according to claim 3, wherein the first tangential axis and the second tangential axis extend in parallel with respect to each other.

6. The tubing set according to claim 3, wherein the first tangential axis and the second tangential axis are displaced with respect to each other in a direction transverse to the longitudinal axis and transverse to both the first and the second tangential axis.

7. The tubing set according to claim 1, wherein the at least one chamber element comprises a bottom wall and a top wall which are displaced with respect to each other along the longitudinal axis and, together with the circumferential wall, define the flow chamber, wherein the inlet port is arranged on the circumferential wall at the bottom wall and the outlet port is arranged on the circumferential wall at the top wall.

8. The tubing set according to claim 7, wherein the bottom wall is part of a first housing part and the top wall is part of a second housing part joined together with the first housing part.

9. The tubing set according to claim 1, wherein the circumferential wall at an outer side facing away from the flow chamber comprises a flat face for positioning an infrared sensor element on the at least one chamber element.

10. The tubing set according to claim 9, wherein the circumferential wall, at the flat face, comprises a reduced wall thickness as compared to at least one other portion of the circumferential wall.

11. The tubing set according to claim 1, wherein the measurement device comprises a handle for manually grabbing the measurement device.

12. The tubing set according to claim 1, wherein the measurement device comprises a first chamber element and a second chamber element connected to each other, wherein the first chamber element is connected to a first inlet-side tube section and a first outlet-side tube section and the second chamber element is connected to a second inlet-side tube section and a second outlet-side tube section.

13. The tubing set according to claim 12, wherein the chamber elements each have a cylindrical shape and a longitudinal axis and extend with the longitudinal axes in parallel to each other.

14. The tubing set according to claim 12, wherein the chamber elements are integrally connected to each other via webs extending in between the chamber elements.

* * * * *